United States Patent [19]

Janssen et al.

[11] Patent Number: 5,278,345
[45] Date of Patent: Jan. 11, 1994

[54] USE OF ECR-1, MAZMORITE AND ECR-18 IN THE CONVERSION OF OXYGENATES TO HYDROCARBONS

[75] Inventors: Marcel J. G. Janssen, Houston, Tex.; David E. W. Vaughan, Flemington, N.J.

[73] Assignee: Exxon Chemical Patents Inc., Linden, N.J.

[21] Appl. No.: 888,668

[22] Filed: May 27, 1992

[51] Int. Cl.$^5$ ............................................. C07C 1/00
[52] U.S. Cl. ................................. 585/640; 585/638; 585/639
[58] Field of Search ...................... 585/638, 639, 640

[56] References Cited

U.S. PATENT DOCUMENTS

| | | |
|---|---|---|
| 3,928,483 | 12/1975 | Chang et al. . |
| 4,025,575 | 5/1977 | Chang et al. . |
| 4,401,637 | 8/1983 | Marosi et al. ..................... 585/640 |
| 4,423,273 | 12/1983 | Hoelderich et al. ............... 585/640 |
| 4,447,669 | 5/1984 | Harmon et al. . |
| 4,467,133 | 8/1984 | Chang et al. ..................... 585/733 |
| 4,496,786 | 1/1985 | Santilli et al. . |
| 4,499,314 | 2/1985 | Seddon et al. . |
| 4,544,793 | 10/1985 | Okado et al. ..................... 585/640 |
| 4,547,616 | 10/1985 | Avidan et al. . |
| 4,579,994 | 4/1986 | Kiyozumi et al. ................. 585/640 |
| 4,657,748 | 4/1987 | Vaughan et al. . |
| 4,661,332 | 4/1987 | Vaughan et al. . |
| 4,677,243 | 6/1987 | Kaiser . |
| 4,698,449 | 10/1987 | Imai et al. ....................... 585/640 |
| 4,843,183 | 6/1989 | Inui . |
| 4,892,721 | 1/1990 | Leonowicz et al. . |
| 5,013,536 | 5/1991 | Vaughan et al. . |

OTHER PUBLICATIONS

Vaughan, D. E. W. et al., "Synthesis of the New Large-Pore Zeolite ECR-1," in *Zeolite Synthesis* (Ocelli, M. L. et al. eds, ACS Press, 1989).

Vaughan, D. E. W. et al., "Characterization of the New Zeolite ECR-1," in *Zeolite Synthesis*, (Ocelli, M. L. et al. eds, ACS Press, 1989).

*Primary Examiner*—Patrick P. Garvin
*Assistant Examiner*—E. D. Irzinski
*Attorney, Agent, or Firm*—Linda K. Russell

[57] ABSTRACT

A process for converting an oxygenate feed to light olefins using a microporous zeolite catalysts such as ECR-1, mazmorites, and/or ECR-18 is provided. In a preferred embodiment, the process is conducted at approximately 440° C. (824° F.) to about 460° C. (860° F.) using a methanol:water (approximately 1:4 molar ratio) feed and results in superior production of light olefins.

66 Claims, No Drawings

USE OF ECR-1, MAZMORITE AND ECR-18 IN THE CONVERSION OF OXYGENATES TO HYDROCARBONS

BACKGROUND OF THE INVENTION

This invention relates to a process for using microporous solid catalysts to convert oxygenates into hydrocarbons and, more particularly, relates to a process for converting alcohols into light olefins using ECR-1, mazmorite, or ECR-18 catalysts.

Light olefins have traditionally been produced through the process of steam or catalytic cracking. Because of the limited availability and high cost of petroleum sources, the cost of producing light olefins from such petroleum sources has been steadily increasing. Many raise the dire prediction of significant oil shortages in the not-too-distant future. Curtailment in the availability of inexpensive petroleum raw materials threatens the supply of light olefins. Light olefins serve as feeds for the production of numerous chemicals.

The search for alternative materials for light olefin production has led to the use of oxygenates such as alcohols, and more particularly to methanol, ethanol, and higher alcohols or their derivatives. These alcohols may be produced by fermentation or from synthesis gas. Synthesis gas can be produced from natural gas, petroleum liquids, carbonaceous materials, including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite catalysts are known to promote the conversion of oxygenates to hydrocarbon mixtures. Numerous patents describe this process for various types of zeolite catalysts: U.S. Pat. Nos. 3,928,483, 4,025,575, 4,252,479 (Chang et al.); 4,496,786 (Santilli et al.); 4,547,616 (Avidan et al.); 4,677,243 (Kaiser); 4,843,183 (Inui); 4,499,314 (Seddon et al.); and 4,447,669 (Harmon et al.). However, none of these patents teach the conversion of oxygenates to hydrocarbons using the type of zeolite catalysts described herein.

These and other disadvantages of the prior art are overcome by the present invention, however, and a new improved process for conversion of oxygenates to hydrocarbons using synthetic zeolites such as ECR-1, mazmorites, and paulingite-type (such as ECR-18) zeolite catalysts is provided.

SUMMARY OF THE INVENTION

In accordance with the present invention, an oxygenate feed is catalytically converted to hydrocarbons rich in light olefins by contacting this feed with synthetic mazmorite-type and/or synthetic paulingite-type zeolite catalysts. In a preferred embodiment, methanol is employed as an oxygenate feed for conversion to hydrocarbons rich in light olefins by contacting this feed with ECR-1, mazmorites, and/or ECR-18. Other oxygenate feeds may be for example, but are not limited to, dimethyl ether, ethanol, isopropanol, n-propanol or mixtures thereof. Further, a diluent may be part of the feed and may comprise water, nitrogen ($N_2$), hydrogen ($H_2$), or other hydrocarbons, including but not limited to paraffins, olefins and aromatics.

It is an object of the present invention to provide a process for producing a hydrocarbon mixture, comprising, contacting an oxygenate feed with a microporous zeolite catalyst, wherein said zeolite is selected from ECR-1, mazmorites, synthetic paulingite-type, ECR-18, or mixtures thereof, to produce a hydrocarbon mixture.

These and other advantages of the present invention will become apparent from the following detailed description.

DETAILED DESCRIPTION OF THE INVENTION

The present invention employs ECR-1, mazmorite and/or synthetic paulingite-type (such as ECR-18) microporous zeolite catalysts to convert oxygenate feeds to hydrocarbons. Zeolites are microporous, crystalline-hydrated aluminosilicates of Group I and II elements interconnected through shared oxygen atoms. The rigid three-dimensional framework of silica and alumina creates a tetrahedral-shaped block which forms the primary building unit of the zeolites. Because the oxygen atoms in zeolites are shared between tetrahedra, the framework possesses a net negative charge. The net negative charge is balanced by exchangeable cations in the crystalline structure, leading to the representation:

$$M_{x/n} [(AlO_2)_x (SiO_2)_y] \cdot zH_2O$$

where M is the cation, n is the cation charge, and z represents the water of hydration. The silica-to-alumina ratio is governed by the amounts of alumina "x" and silica "y" comprising the zeolite. When M is a proton, the zeolite acquires the characteristics of a Broensted acid.

The zeolites generally have ordered, porous crystalline structures containing a small number of cavities that are interconnected by a number of still smaller channels. The cavities and channels are uniform in size within a certain type of zeolitic material. The dimensions of the pores or cavities allow for adsorption of molecules of certain dimensions while excluding molecules of larger dimensions. The crystal structure of zeolites provides a selective, constrained access to and egress from the intracrystalline free space. This phenomenon, also called "shape-selective catalysis," derives from zeolite geometry.

An important component of zeolite geometry derives from the proportions of silicon and aluminum atoms comprising the tetrahedra. The molar ratio of silica-to-alumina may be determined by conventional analysis such as wet chemical analysis (e.g., atomic absorption spectrometry or inductively coupled plasma emission spectroscopy) or by the stoichiometry of silica and alumina used in zeolite synthesis. This ratio is meant to represent, as closely as possible, the silica-to-alumina ratio in the rigid anionic framework of the zeolite crystal. Aluminum in the binder or in cationic or other form within the porous channels is not considered in calculating the silica-to-alumina ratio.

The catalytic and adsorptive properties of the zeolite may also be varied by changing the ions within the catalyst. Conventional ion exchange techniques may be used to change the cations. There are a large number of both natural and synthetic zeolitic structures. The enormity of zeolite structural permutations can be understood by considering the book *Atlas of Zeolite Structures* by W. M. Meier and D. H. Olson.

The feedstock flow rate affects olefin production. Increasing the feedstock flow rate (expressed as weight hourly space velocity, or WHSV) enhances the formation of olefin production relative to paraffin production. However, the enhanced olefin production relative to paraffin production is offset by a diminished conversion of oxygenate to hydrocarbons.

ECR-1 is a 12-ring synthetic zeolite. It is formed by using bis (2-hydroxyethyl) dimethylammonium or bis (2-hydroxypropyl) dimethylammonium as an organic template. ECR-1 is described more fully in U.S. Pat. No. 4,657,748, which is incorporated herein by reference. ECR-1 has a silica-to-alumina (Si/Al$_2$) molar ratio of about 5–20, and usually about 7, comparable to naturally occurring mazzite. ECR-1 has a recurrent twin structure comprising component sheets structurally characteristic of naturally occurring mordenite (which normally has a silica-to-alumina molar ratio of greater than 10) and mazzite. Thus ECR-1 represents a novel, complex synthetic zeolite having structural similarities to both these existing natural zeolites.

Materials similar and related to ECR-1 include the mazmorites, described in U.S. Pat. No. 4,892,721, and incorporated herein by reference. The mazmorites are complex intergrown synthetic permutations of ECR-1.

ECR-18 is structurally similar to the natural mineral paulingite. Paulingite is a very rare mineral classified as a member of the faujasite group. ECR-18 is produced using a tetraethylammonium template. It is described in more detail in U.S. Pat. Nos. 4,661,332 and 5,013,536 which are incorporated herein by reference. Like ECR-1, ECR-18 is a novel, complex synthetic zeolite having structural similarities to naturally occurring zeolites. The pore size and adsorptive capacities of these synthetic ECR zeolites are nevertheless different from the natural zeolites.

In accordance with the process of the present invention, an oxygenate feed is catalytically converted to hydrocarbons containing aliphatic moieties such as, but not limited to, methane, ethane, ethylene, propane, propylene and other higher aliphatics and aromatics, by contacting the oxygenate feed with a preselected zeolite catalyst. The oxygenate feed comprises hydrocarbons containing aliphatic moieties such as, but not limited to, alcohols, halides, mercaptans, sulfides, amines, ethers and carbonyl compounds or mixtures thereof. The aliphatic moiety preferably contains from about 1 to about 10 carbon atoms, and more preferably 1 to 4 carbon atoms. Representative oxygenates include, but are not limited to methanol, isopropanol, n-propanol, ethanol, fuel alcohols, dimethyl ether, diethyl ether, methyl mercaptan, methyl sulfide, methyl amine, ethyl mercaptan, ethylchloride, formaldehyde, dimethylketone, acetic acid, n-alkylamines, n-alkylhalides, and n-alkylsulfides having alkyl groups of 1 to 10 carbon atoms or mixtures thereof. In a preferred embodiment, methanol is used as the oxygenate feed. The term "oxygenate feed" as employed in the present invention and described herein designates only the organic material used as the feed. The total charge of feed to the reaction zone may contain additional compounds such as diluents.

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include, but are not limited to, helium, argon, nitrogen, carbon monoxide, carbon dioxide, hydrogen, water, paraffins, hydrocarbons (such as methane and the like), aromatic compounds, or mixtures thereof. Use of an aqueous diluent as part of the feed imparts as a non-limiting example a hydrocarbon fraction rich in light olefins. In an alternative embodiment of the present invention, the feed comprises an oxygenate:water feed having an approximate 1:4 molar ratio, most preferably a methanol:water feed having an approximate 1:4 molar ratio. Even though the process described herein may employ a diluent, computable quantities of the oxygenate feed (i.e., composition and weight hourly space velocity (WHSV)) are to be computed as an essentially diluent-free oxygenate feed unless otherwise stated.

The process of the present invention is preferably conducted in the vapor phase such that the oxygenate feed is contacted in a vapor phase in a reaction zone with the zeolite catalyst at effective process conditions to produce hydrocarbons, i.e., an effective temperature, pressure, WHSV and, optionally, an effective amount of diluent, correlated to produce hydrocarbons. Alternatively, the process may be conducted in a liquid phase.

When the process is carried out in the liquid phase the process necessarily involves the separation of products formed in a liquid reaction media and can result in different conversions and selectivities of feedstock-to-product with respect to the relative ratios of the light olefin products as compared to that formed by the vapor phase process.

The process is effectively carried out over a wide range of pressures, including autogenous pressures. At pressures between about 0.001 atmospheres (0.76 torr) and about 1000 atmospheres (760,000 torr), the formation of light olefin products will be effected although the optimum amount of product will not necessarily form at all pressures. The preferred pressure is between about 0.01 atmospheres (7.6 torr) and about 100 atmospheres (76,000 torr). The pressures referred to herein for the process are exclusive of the inert diluent, if any, that is present, and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum, although light olefin such as ethylene may still be formed.

The process is effected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected.

The temperature which may be employed in the process may vary over a wide range depending, at least in part, on the selected molecular sieve catalyst. In general, the process can be conducted at an effective temperature between about 200° C. (392° F.) and about 700° C. (1292° F.). Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. (392° F.) and about 700° C. (1292° F.).

The processes employing ECR-1 for conversion of an oxygenate feed to hydrocarbons are conducted at temperatures of approximately 350° C. (662° F.) to about 550° C. (1022° F.), preferably about 400° C. (752° F.) to about 500° C. (932° F.), and more preferably about 440° C. (824° F.) to about 460° C. (860° F.). The WHSV of these processes is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$ At 0.8 hr.$^{-1}$ to 1.2 hr.$^{-1}$ WHSV, approximately 95% to 100% conversion of oxygenate feed to hydrocarbons occurs.

The processes employing mazmorite for conversion of an oxygenate feed to hydrocarbons are conducted at temperatures of approximately 350° C. (662° F.) to about 550° C. (1022° F.), preferably about 400° C. (752° F.) to about 500° C. (932° F.), and more preferably about 440° C. (824° F.) to about 460° C. (860° F.). The WHSV of these processes is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$ At 0.8 hr.$^{-1}$ to 1.2 hr.$^{-1}$ WHSV, approximately 95% to 100% conversion of oxygenate feed to hydrocarbons occurs.

The processes employing a synthetic paulingite-type zeolite catalyst for conversion of an oxygenate feed to hydrocarbons are conducted at temperatures of approximately 350° C. (662° F.) to about 550° C. (1022° F.), preferably about 400° C. (752° F.) to about 500° C. (932° F.), and more preferably about 440° C. (824° F.) to about 460° C. (860° F.). The WHSV of these processes is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$ At 0.8 hr.$^{-1}$ to 1.2 hr.$^{-1}$ WHSV, approximately 95% to 100% conversion of oxygenate feed to hydrocarbons occurs. More specifically, the processes employing ECR-18 for conversion of an oxygenate feed to hydrocarbons are conducted at temperatures of approximately 350° C. (662° F.) to about 550° C. (1022° F.), preferably about 400° C. (752° F.) to about 500° C. (932° F.), and more preferably about 440° C. (824° F.) to about 460° C. (860° F.). The WHSV of these processes is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$ At 0.8 hr.$^{-1}$ to 1.2 hr.$^{-1}$ WHSV, approximately 95% to 100% conversion of oxygenate feed to hydrocarbons occurs.

The processes for conversion of an oxygenate feed to hydrocarbons may be conducted using mixtures of ECR-1, mazmorite, synthetic paulingite-type zeolite and ECR-18 as would be determined by a person having ordinary skill in the art. The processes using mixtures are conducted at temperatures of approximately 350° C. (662° F.) to about 550° C. (1022° F.), preferably about 400° C. (752° F.) to about 500° C. (932° F.), and more preferably about 440° C. (824° F.) to about 460° C. (860° F.). The WHSV of these processes is approximately 0.01 hr.$^{-1}$ to about 100 hr.$^{-1}$, preferably about 0.1 hr.$^{-1}$ to about 10 hr.$^{-1}$, and more preferably about 0.8 hr.$^{-1}$ to about 1.2 hr.$^{-1}$ At 0.8 hr.$^{-1}$ to 1.2 hr.$^{-1}$ WHSV, approximately 95% to 100% conversion of oxygenate feed to hydrocarbons occurs.

The following examples serve to illustrate specific embodiments of the process of this invention, but should not be considered as a limitation on the scope of the invention.

EXAMPLE 1

A synthetic ECR-1 zeolite catalyst was produced as described in U.S. Pat. No. 4,657,748. The ECR-1 described in this example had a silica-to-alumina molar ratio of 7:1, determined by chemical analysis. ECR-1 was calcined at 510° C. (950° F.) to remove the template and the calcined material was ion-exchanged with an ammonium-nitrate solution (85° C., 185° F.; 12 hrs.). Generally, the ion exchange was repeated two or three times, with a calcination at 510° C. (950° F.) between each ion exchange step. The catalytic conversion of oxygenate to hydrocarbons was conducted at 450° C. (842° F.) and at a WHSV of 1.0 hr.$^{-1}$. The feed consisted of a mixture of methanol:water (approximately 1:4 molar ratio).

The catalytic conversion of methanol to hydrocarbons was carried out in a fixed bed (½", 1.27 cm diameter), stainless steel reactor having three spaced zones and equipped with a ⅛" (0.32 cm) coiled preheater. In addition, the reactor was equipped with a ⅛" (0.32 cm) thermocouple well running axially through the reactor. The reactor was inserted into and heated in an Applied Test Systems 3 zone tube furnace (12", 30.5 cm long; 1 ¼", 3.18 cm I.D.). The first reactor zone is used as a preheater zone; the catalyst bed is heated in the second reactor zone. The third zone operates as a quench zone maintained at a temperature of about 200° C. (392° F.) to about 300° C. (572° F.).

Generally, 2 grams (0.07 ounces) catalyst ($-14/+20$ mesh) were mixed with 2.5 grams (0.09 ounces) of quartz ($-20/+60$ mesh); the first and third zones of the reactor were filled with quartz chips ($-10/+20$ mesh). To improve the heat transfer between the second reactor zone (containing the catalyst bed) and the furnace heating coils, the second reactor zone was equipped with a cylindrical ($\sim 4$", 10.2 cm long; 1 ¼", 3.18 cm O.D.) aluminum or stainless steel block. This block contained a central hole for a thermocouple well in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the bottom of the reactor was analyzed on line for (i) carbon monoxide; carbon dioxide; water; dimethyl ether; methanol; $C_1$–$C_3$ hydrocarbons, including ethylene ($C_2=$), propylene ($C_3=$), and other products (such as $C_4$ and higher hydrocarbons) with a Porepack Q (capillary column gas chromatography) column using a thermal conductivity detector and (ii) $C_1$–$A_{10}$ hydrocarbons with a DB-1 (capillary column gas chromatography) column using a flame ionization detector. Product distribution was:

| Hydrocarbon | Hydrocarbon distribution (Wt %, Excluding $H_2O$) |
| --- | --- |
| $CH_4$ | 33 |
| $C_2=$ | 27 |
| $C_3=$ | 11 |
| $C_2 + C_3$ | 24 |

| Hydrocarbon | Hydrocarbon distribution (Wt %, Excluding H$_2$O) |
|---|---|
| Other | 5 |

EXAMPLE 2

A synthetic paulingite-type zeolite catalyst (ECR-18) was produced as described in U.S. Pat. No. 5,013,536. The ECR-18 described in this example had a silica-to-alumina molar ratio of 6.4 as determined by wet chemical analysis. ECR-18 was calcined at 510° C. (950° F.) and the calcined material was ion-exchanged with an ammonium-nitrate solution (85° C., 185° F.; 12 hrs.). Generally, the ion exchange was repeated two or three times, with a calcination at 510° C. (950° F.) between each ion exchange step. The catalytic conversion of oxygenate to hydrocarbons was conducted at 450° C. (842° F.) and at a WHSV of 1.0 hr.$^{-1}$. The feed consisted of a mixture of methanol:water (approximately 1:4 molar ratio).

The catalytic conversion of methanol to hydrocarbons was carried out in a fixed bed ($\frac{1}{2}$", 1.27 cm diameter), stainless steel reactor, equipped with a $\frac{1}{8}$" (0.32 cm) coiled preheater. In addition, the reactor was equipped with a $\frac{1}{8}$" (0.32 cm) thermocouple well running axially through the reactor. The reactor was inserted into and heated in an Applied Test Systems 3 zone tube furnace (12", 30.5 cm long; 1 $\frac{1}{4}$", 3.18 cm I.D.). The first reactor zone is used as a preheater zone; the catalyst bed is heated in the second reactor zone. The third zone operates as a quench zone maintained at a temperature of about 200° C. (392° F.) to about 300° C. (572° F.).

Generally, 2 grams (0.07 ounces) catalyst ($-14/+20$ mesh) were mixed with 2.5 grams (0.09 ounces) of quartz ($-20/+60$ mesh); the first and third zones of the reactor were filled with quartz chips ($-10/+20$ mesh). To improve the heat transfer between the second reactor zone (containing the catalyst bed) and the furnace heating coils, the second reactor zone was equipped with a cylindrical ($\sim 4$", 10.2 cm long; 1 $\frac{1}{4}$", 3.18 cm O.D.) aluminum or stainless steel block. This block contained a hole for a thermocouple well in order to be able to measure the block temperature.

Gas flows were controlled by mass flow controllers, while liquid feed rates were controlled by a Beckmann 114M pump or a Sage 341B syringe pump.

The product emerging from the reactor was analyzed on line for (i) carbon monoxide; carbon dioxide; water; dimethyl ether; methanol; C$_1$-C$_3$ hydrocarbons, including ethylene (C$_2$=), propylene (C$_3$=) and other hydrocarbon (C$_4$ and higher) products with a Porepack Q (capillary column gas chromatography) column using a thermal conductivity detector and (ii) C$_1$-A$_{10}$ hydrocarbons with a DB-1 (capillary column gas chromatography) column using a flame ionization detector. Product distribution was:

| Hydrocarbon | Hydrocarbon distribution (Wt %, Excluding H$_2$O) |
|---|---|
| CH$_4$ | 7 |
| C$_2$= | 38 |
| C$_3$= | 30 |
| C$_2$ + C$_3$ | 7 |
| Other | 18 |

Thus, it may be seen that the present invention provides a process for producing light olefins from an oxygenate feed by catalytically converting such oxygenate to olefins by contacting such oxygenate with an ECR-1, mazmorite, or ECR-18 catalyst.

Many other variations and modifications may be made in the techniques hereinbefore described, by those having experience in this technology, without departing from the concept of the present invention. Accordingly, it should be clearly understood that the methods described in the foregoing description are illustrative only and not intended as limitations on the scope of the invention.

What is claimed is:

1. A process for producing a hydrocarbon mixture comprising: contacting a methanol:water (approximately 1:4 molar ratio) feed with zeolite ECR-1 at a temperature of from about 440° C. (824° F.) to about 460° C. (860° F.), a weight hourly space velocity of about 0.8 hr.$^{-1}$ to about 1.2 hr.$^{-1}$ and a pressure of between about 0.01 atmospheres (7.6 torr) and 100 atmospheres (76,000 torr) to produce a hydrocarbon mixture.

2. A process for producing a hydrocarbon mixture comprising: contacting a methanol:water (approximately 1:4 molar ratio) feed with zeolite ECR-18 at a temperature of from about 440° C. (824° F.) to about 460° C. (860° F.), a weight hourly space velocity of about 0.8 hr.$^{-1}$ to about 1.2 hr.$^{-1}$ and a pressure of between about 0.01 atmospheres (7.6 torr) and 100 atmospheres (76,000 torr) to produce a hydrocarbon mixture.

3. A process for producing a hydrocarbon mixture containing substantially only light olefins comprising: contacting zeolite ECR-1 with a feed comprising oxygenates or hydrocarbons selected from the group consisting of halides, mercaptans, sulfides, and amines, to produce a hydrocarbon mixture containing substantially only light olefins.

4. A process according to claim 3 wherein the light olefins are selected from the group consisting of ethylene and propylene.

5. A process according to claim 3 wherein the process is conducted at a temperature of from about 350° C. (662° F.) to about 550° C. (1022° F.).

6. A process according to claim 3 wherein the process is conducted at a temperature of from about 400° C. (752° F.) to about 500° C. (932° F.).

7. A process according to claim 3 wherein the process is conducted at a temperature of from about 440° C. (824° F) to about 460° C. (860° F.).

8. A process according to claim 3 wherein the process is conducted at a weight hourly space velocity of approximately 0.091 hr.$^{-1}$ to about 100 hr.$^{-1}$.

9. A process according to claim 3 wherein the process is conducted at a weight hourly space velocity of about 0.8 hr.$^{-1}$ to about 10 hr.$^{-1}$.

10. A process according to claim 3 wherein the process is conducted at a weight hourly space velocity of about 0.8 hr.$^{-1}$ to about 1.2 hr.$^{-1}$.

11. A process according to claim 3 wherein the process is conducted at a pressure between about 0.001 atmospheres (0.76 torr) and about 1000 atmospheres (760,000 torr).

12. A process according to claim 3 wherein the process is conducted at a pressure between about 0.01 atmospheres (7.6 torr) and 100 atmospheres (76,000 torr).

13. A process according to claim 3 wherein the feed is an oxygenate selected from the group consisting of methanol, dimethyl ether, diethyl ether, isopropanol, n-propanol, ethanol, and fuel alcohols, or mixtures thereof.

14. A process according to claim 3 wherein the feed comprises methanol.

15. A process according to claim 3 wherein the oxygenate feed also includes a diluent.

16. A process according to claim 15 wherein the diluent is selected from the group consisting of helium, argon, nitrogen, carbon monoxide, carbon dioxide, hydrogen, water, paraffins, hydrocarbons, and aromatics, or mixtures thereof.

17. A process according to claim 15 wherein the diluent is water.

18. A process according to claim 17 wherein the molar ratio of oxygenate feed to water is approximately 1.4.

19. A process for producing a hydrocarbon mixture containing substantially only light olefins comprising: contacting a mazmorite with a feed comprising oxygenates or hydrocarbons selected from the group consisting of halides, mercaptans, sulfides, and amines, to produce a hydrocarbon mixture containing substantially only light olefins.

20. A process according to claim 19 wherein the light olefins are selected from the group consisting of ethylene and propylene.

21. A process according to claim 19 wherein the process is conducted at a temperature of from about 350° C. (662° F.) to about 550° C. (1022° F.).

22. A process according to claim 19 wherein the process is conducted at a temperature of from about 400° C. (752° F.) to about 500° C. (932° F.).

23. A process according to claim 19 wherein the process is conducted at a temperature of from about 440° C. (824° F.) to about 460° C. (860° F.).

24. A process according to claim 19 wherein the process is conducted at a weight hourly space velocity of approximately 0.091 hr.$^{-1}$ to about 100 hr.$^{-1}$.

25. A process according to claim 19 wherein the process is conducted at a weight hourly space velocity of about 0.8 hr.$^{-1}$ to about 10 hr.$^{-1}$.

26. A process according to claim 19 wherein the process is conducted at a weight hourly space velocity of about 0.8 hr.$^{-1}$ to about 1.2 hr.$^{-1}$.

27. A process according to claim 19 wherein the process is conducted at a pressure between about 0.001 atmospheres (0.76 torr) and about 1000 atmospheres (760,000 torr).

28. A process according to claim 19 wherein the process is conducted at a pressure between about 0.01 atmospheres (7.6 torr) and 100 atmospheres (76,000 torr).

29. A process according to claim 19 wherein the feed is an oxygenate selected from the group consisting of methanol, dimethyl ether, diethyl ether, isopropanol, n-propanol, ethanol and fuel alcohols, or mixtures thereof.

30. A process according to claim 19 wherein the feed comprises methanol.

31. A process according to claim 19 wherein the oxygenate feed also includes a diluent.

32. A process according to claim 31 wherein the diluent is selected from the group consisting of helium, argon, nitrogen, carbon monoxide, carbon dioxide, hydrogen, water, paraffins, hydrocarbons, and aromatics, or mixtures thereof.

33. A process according to claim 31 wherein the diluent is water.

34. A process according to claim 33 wherein the molar ratio of oxygenate feed to water is approximately 1:4.

35. A process for producing a hydrocarbon mixture containing substantially only light olefins comprising: contacting synthetic paulingite catalysts with a feed comprising oxygenates or hydrocarbons selected from the group consisting of halides, mercaptans, sulfides, and amines, to produce a hydrocarbon mixture containing substantially only light olefins.

36. A process according to claim 35 wherein the light olefins are selected from the group consisting of ethylene and propylene.

37. A process according to claim 35 wherein the process is conducted at a temperature of from about 350° C. (662° F.) to about 550° C. (1022° F.).

38. A process according to claim 35 wherein the process is conducted at a temperature of from about 400° C. (752° F.) to about 500° C. (932° F.).

39. A process according to claim 35 wherein the process is conducted at a temperature of from about 440° C. (824° F.) to about 460° C. (860° F.).

40. A process according to claim 35 wherein the process is conducted at a weight hourly space velocity of approximately 0.091 hr.$^{-1}$ to about 100 hr.$^{-1}$.

41. A process according to claim 35 wherein the process is conducted at a weight hourly space velocity of about 0.8 hr.$^{-1}$ to about 10 hr.$^{-1}$.

42. A process according to claim 35 wherein the process is conducted at a weight hourly space velocity of about 0.8 hr.$^{-1}$ to about 1.2 hr.$^{-1}$.

43. A process according to claim 35 wherein the process is conducted at a pressure between about 0.001 atmospheres (0.76 torr) and about 1000 atmospheres (760,000 torr).

44. A process according to claim 35 wherein the process is conducted at a pressure between about 0.01 atmospheres (7.6 torr) and 100 atmospheres (76,000 torr).

45. A process according to claim 35 wherein the feed is an oxygenate selected from the group consisting of methanol, dimethyl ether, diethyl ether, isopropanol, n-propanol, ethanol, and fuel alcohols, or mixtures thereof.

46. A process according to claim 35 wherein the feed comprises methanol.

47. A process according to claim 35 wherein the oxygenate feed also includes a diluent.

48. A process according to claim 47 wherein the diluent is selected from the group consisting of helium, argon, nitrogen, carbon monoxide, carbon dioxide, hydrogen, water, paraffins, hydrocarbons, and aromatics, or mixtures thereof.

49. A process according to claim 47 wherein the diluent is water.

50. A process according to claim 47 wherein the molar ratio of oxygenate feed to water is approximately 1:4.

51. A process for producing a hydrocarbon mixture containing substantially only light olefins comprising: contacting a calcined zeolite ECR-18 with a feed comprising oxygenates or hydrocarbons selected from the group consisting of halides, mercaptans, sulfides, and amines, to produce a hydrocarbon mixture containing substantially only light olefins.

52. A process according to claim 51 wherein the light olefins are selected from the group consisting of ethylene and propylene.

53. A process according to claim 51 wherein the process is conducted at a temperature of from about 350° C. (662° F.) to about 550° C. (1022° F.).

54. A process according to claim 51 wherein the process is conducted at a temperature of from about 400° C. (752° F.) to about 500° C. (932° F.).

55. A process according to claim 51 wherein the process is conducted at a temperature of from about 440° C. (824° F.) to about 460° C (860° F.).

56. A process according to claim 51 wherein the process is conducted at a weight hourly space velocity of approximately 0.091 hr.$^{-1}$ to about 100 hr.$^{-1}$.

57. A process according to claim 51 wherein the process is conducted at a weight hourly space velocity of about 0.8 hr.$^{-1}$ to about 10 hr.$^{-1}$.

58. A process according to claim 51 wherein the process is conducted at a weight hourly space velocity of about 0.8 hr.$^{-1}$ to about 1.2 hr.$^{-1}$.

59. A process according to claim 51 wherein the process is conducted at a pressure between about 0.001 atmospheres (0.76 torr) and about 1000 atmospheres (760,000 torr).

60. A process according to claim 51 wherein the process is conducted at a pressure between about 0.01 atmospheres (7.6 torr) and 100 atmospheres (76,000 torr).

61. A process according to claim 51 wherein the feed is an oxygenate selected from the group consisting of methanol, dimethyl ether, diethyl ether, isopropanol, n-propanol, ethanol, and fuel alcohols, or mixtures thereof.

62. A process according to claim 51 wherein the feed comprises methanol.

63. A process according to claim 51 wherein the oxygenate feed also includes a diluent.

64. A process according to claim 63 wherein the diluent is selected from the group consisting of helium, argon, nitrogen, carbon monoxide, carbon dioxide, hydrogen, water, paraffins, hydrocarbons, and aromatics, or mixtures thereof.

65. A process according to claim 63 wherein the diluent is water.

66. A process according to claim 65 wherein the molar ratio of oxygenate feed to water is approximately 1:4.

* * * * *